United States Patent [19]

Honjo et al.

[11] Patent Number: 5,416,201
[45] Date of Patent: May 16, 1995

[54] DNAS THAT CODE FOR MOUSE INTERLEUKEN 4

[75] Inventors: Tasuku Honjo, No. 13-12, Ueno-higashi 3-chome, Toyonaka-shi, Osaka; Eva Severinson, Bengt Ekehielmsg. 13, S-116 48 Stockholm, both of Stockholm, Sweden

[73] Assignee: Tasuku Honjo, Osaka, Japan

[21] Appl. No.: 913,276

[22] Filed: Sep. 30, 1986

[30] Foreign Application Priority Data

Sep. 30, 1985 [JP] Japan .................. 60-214870

[51] Int. Cl.⁶ .................. C12P 21/02; C12P 19/34; C12N 15/00; C12N 1/21; C07K 3/00; C07H 15/12; A61K 37/02

[52] U.S. Cl. .................. 536/23.5; 435/69.1; 435/69.51; 435/172.3; 435/252.33; 435/320.1; 530/300; 530/350; 935/10; 935/18; 935/29; 935/41; 935/56; 935/73

[58] Field of Search .................. 435/68, 70, 172.3, 91; 530/300, 351, 324, 326; 536/27; 935/69.1, 69.51, 172.3, 252.35, 320.1, 10, 18, 29, 41, 56, 73

[56] References Cited

FOREIGN PATENT DOCUMENTS 0218432 4/1987 European Pat. Off. .
8489019 12/1985 Japan .................. C12N 15/00
PCT8702990 5/1987 WIPO .

OTHER PUBLICATIONS

Sideras et al. Eur. J. Immunol. 1985(15) 593-598.
Lee, F. et al, Proc. Natl. Acad. Sci. USA, 83:2061-2065 (1986).
Noma, Y. et al., Nature, 319:640-646 (1986).

Primary Examiner—Joan Ellis
Attorney, Agent, or Firm—Sughrue, Mion, Zinn, Macpeak & Seas

[57] ABSTRACT

Mouse $IgG_1$ inducing factor and the DNA that codes for the same were isolated by using a novel genetic technique, and their structures determined by the dideoxy chain termination method. The mouse $IgG_1$ inducing factor obtained by the method of this invention has activity to improve immune response in living bodies and are hence useful for the treatment and prevention of infectious diseases, AIDS, functional immunodeficiency and the like. This factor, or part of its amino acid sequence, may also be used for the preparation of antibody against the same. In addition, it is possible to use this factor as a model for the synthesis of other polypeptides having similar structures, and for many other purposes.

5 Claims, 3 Drawing Sheets

FIG. 4

```
GGATCCCCGGGCGAGCTGGGGGGGGAT TTGTTAGCATCTCTTGATAAACTTAATTGTCT
BamHI                     1
                          1    Met Gly Leu Asn Pro Gln Leu Val
CTCGTCACTGACGGCACAGAGCTATTG    ATG GGT CTC AAC CCC CAG CTA GTT
              50                                         20
Val Ile Leu Leu Phe Phe Leu Glu Cys Thr Arg Ser His Ile His
GTC ATC CTG CTC TTC TTT CTC GAA TGT ACC AGG AGC CAT ATC CAC
                   100          Rsa I
Gly Cys Asp Lys Asn His Leu Arg Glu Ile Ile Gly Ile Leu Asn
GGA TGC GAC AAA AAT CAC TTG AGA GAG ATC ATC GGC ATT TTG AAC
         40                150
Glu Val Thr Gly Glu Gly Thr Pro Cys Thr Glu Met Asp Val Pro
GAG GTC ACA GGA GAA GGG ACG CCA TGC ACG GAG ATG GAT GTG CCA
                       60      200
Asn Val Leu Thr Ala Thr Lys Asn Thr Thr Glu Ser Glu Leu Val
AAC GTC CTC ACA GCA ACG AAG AAC ACC ACA GAG AGT GAG CTC GTC
                           250         80  Sac I
Cys Arg Ala Ser Lys Val Leu Arg Ile Phe Tyr Leu Lys His Gly
TGT AGG GCT TCC AAG GTG CTT CGC ATA TTT TAT TTA AAA CAT GGG
                                                300
Lys Thr Pro Cys Leu Lys Lys Asn Ser Ser Val Leu Met Glu Leu
AAA ACT CCA TGC TTG AAG AAG AAC TCT AGT GTT CTC ATG GAG CTG
    100                                              350 Pst I
Gln Arg Leu Phe Arg Ala Phe Arg Cys Leu Asp Ser Ser Ile Ser
CAG AGA CTC TTT CGG GCT TTT CGA TGC CTG GAT TCA TCG ATA AGC
                       120                              400
Cys Thr Met Asn Glu Ser Lys Ser Thr Ser Leu Lys Asp Phe Leu
TGC ACC ATG AAT GAG TCC AAG TCC ACA TCA CTG AAA GAC TTC CTG
                                                 140
Glu Ser Leu Lys Ser Ile Met Gln Met Asp Tyr Ser END
GAA AGC CTA AAG AGC ATC ATG CAA ATG GAT TAC TCG TAG TACTGAG
450                                                 Rsa I

CCACCATGCTTTAACTTATGAATTTTTAATGGTTTTATTTTTAATATTTATATATTTAT
      500

AATTCATAAAATAAAATATTTGTATAATGT(A)~100
```

DNAS THAT CODE FOR MOUSE INTERLEUKEN 4

BACKGROUND OF THE INVENTION

1. Field of the Invention

This invention relates to novel polypeptides, DNAs that code for the same and method of preparing said polypeptides and DNAs. More particularly, it relates to IgG$_1$ inducing factor, which is one of the T-cell humoral factors playing an important role in the regulation and control of immune response in living bodies, to DNAs that code for the same, and to a method for preparing said factor and DNAs.

It is well known that T cells and B cells participate in the immunological reaction system in living bodies.

B cells differentiate from hematopoietic stem cells into mature B cells having, on the surface of cell membrane, IgM and IgD as antigen receptor. The mature B cells thus formed then propagate by stimulation of specific antigens, eventually differentiating into anti-body producing cells. It is known that this propagation of B cells caused by antigen stimulation requires the action of T-cell-derived humoral factors; Studies are actively under way in many laboratories over the world on these humoral factors by using various cell lines, hybridomas and clones derived from T cells.

These T-cell-derived humoral factors might be divided into the following three groups in terms of activity: the first group containing factors which, by acting before and after stimulation, induces resting B cells into growth cycle or promotes differentiation including class switch recombination; the second group containing factors which serve to maintain such growth of B cells; and the third group containing factors which act upon the B cells propagated by antigen stimulation and by the action of the first and second group factors, forcing them to secrete antibodies.

Cloning the genes of these factors, allowing each gene to establish itself, and studying them individually would provide a powerful means to characterize the physiological functions of each factor and to effectively utilize them as medicines.

2. Description of the Prior Art

The presence of mouse IgG$_1$ inducing factor has already been suggested, but none of known techniques has so far been successful in isolating this factor. For example, when a cells capable of producing said factor is grown, the resultant culture medium contains much impurities and only an extremely small amount of said factor, making its isolation practically impossible. In the technique to isolate mRNA from the cells producing said factor, thereby cloning the objective gene, this cloning operation is extremely difficult because of the minute amount of the objective mRNA and the presence of many other types of mRNA. Thus nothing is known about the structure of said IgG$_1$ inducing factor, not to mention the DNA that codes for this factor.

BRIEF SUMMARY OF THE INVENTION

We have succeeded in cloning the mouse IgG$_1$ inducing factor by using a novel technique (a technique which one of the present inventors has separately filed for patent application), and in determining the structures of said factor and the DNA that codes for the same. This invention was accomplished based on these findings.

DETAILED DESCRIPTION OF THE INVENTION

According to the method of this invention, the gene of mouse IgG$_1$ inducing factor, as well as the mRNA and DNA that code for the same, can be isolated as described below.

mRNAs, which are isolated from B6.C-H-2$^{bm12}$2.19 T cells (10$^9$) previously stimulated by concanavalin A (Con A), are fractionated by the sucrose gradient method, each fraction is translated in oocytes of *Xenopus laevis*, and a fraction containing mRNA that codes for mouse IgG$_1$ inducing factor is collected by measuring the IgG$_1$ inducing factor activity of the translation products (FIG. 1). Using this mRNA as template, a plasmid containing cDNA at a position downstream SP6 promoter (FIG. 2) is synthesized, followed by preparation of a cDNA library. This cDNA library is treated with restriction endonucleases and then subjected to in-vitro transcription using SP6 RNA polymerase to synthesize mRNAs. The mRNAs thus prepared are introduced into oocytes of *Xenopus laevis* and the products are screened in terms of IgG$_1$ inducing factor activity, thereby cloning the gene of said factor from the cDNA library. The DNA that codes for the IgG$_1$ inducing factor is isolated from the clone separated above, and mRNA is obtained by in-vitro transcription using SP6 RNA polymerase. The IgG$_1$ inducing factor (the objective polypeptide) can be produced from this DNA or mRNA by any known technique; for example, by preparing a plasmid carrying the gene of IgG$_1$ inducing factor downstream a suitable eukaryocyte (or prokaryocyte) promoter and introducing it into eukaryotic (or prokaryotic) cells to effect transformation, or by introducing the mRNA into eukaryotic cells (e.g., oocytes of *Xenopus laevis*).

The nucleotide sequence of the DNA was determined by the dideoxy chain termination method using phage M13.

The IgG$_1$ inducing factor obtained by the method of this invention has activity to improve immune response in living bodies and are hence useful for the treatment and prevention of infectious diseases, AIDS, functional immunodeficiency and the like. It is also effective as a medicine for postoperative patients. The suitable dose may vary with the conditions of disease, age and body weight, but it may be intravenously administered in an amount ranging from 0.1μg to 1 mg.

The IgG$_1$ inducing factor, and part of its amino acid sequence, may also be used for the preparation of antibody against the same. In addition, it is possible to use the IgG$_1$ inducing factor as a model for the synthesis of other polypeptides having similar structures. Furthermore, receptors of the IgG$_1$ inducing factor can be isolated by using said factor as ligand.

It is also possible to isolate the genes of IgG$_1$ inducing factors of animals other than mice (including humans) by using, as probe, the DNA that codes for the IgG$_1$ inducing factor obtained by the method of this invention.

EXAMPLE 1

Isolation of T cells capable of producing IgG$_1$ inducing factor

T cells (B6.C-H-2$^{bm12}$2.19 T cells; Kalorinska Laboratories) were suspended in a medium [RPMI-1640 medium containing 5% FCS, 5×10$^{-5}$M 2-mercaptoethanol, and 15% of rat Con A supernatant (culture supernatant of rat splenic cells stimulated by concanavalin A)] and cultured together with mouse B10 splenic cells irradiated by X-ray (2000 R) to effect alloantigen stimulation. The stimulated 2.19 T cells thus obtained were suspended in a medium [RPMI-1640 medium containing 5% FCS, $5 \times 10^{-5}$M 2-mercaptoethanol, and 10% of rat Con A supernatant] at a cell concentration of $1 \times 10^6$/ml, 3 µg/ml Con A was added, and the mixture was incubated at 37° C. for six hours in the presence of 5% $CO_2$. The propagated cells ($10^9$) were collected and stored in frozen state in liquid nitrogen.

EXAMPLE 2

Isolation of mRNA that codes for $IgG_1$ inducing factor

The T cells collected in Example 1 ($10^9$) were broken down and denatured in a guanidium thiocyanate solution (containing 5M guanidium thiocyanate, 25 mM sodium citrate, 0.5% N-lauroylsarcosine sodium salt, and 0.1M 2-mercaptoethanol) by means of a Teflon homogenizer, and the resulting mixture was laid on the surface of 5.7M CsCl-0.1M EDTA solution. Centrifugation at 15° C. using RPS 28A Rotor (Hitachi) at 28000 rpm for 20 hours gave the precipitate of RNA.

This RNA, dissolved in a high-concentration salt solution [containing 0.5M KCl, 10 mM Tris-HCl (pH 7.4) and 0.1 mM EDTA], was absorbed on an oligo-cellulose column, and the absorbed portion was eluted with a low-concentration salt solution [containing 10 mM Tris-HCl (pH 7.4) and 0.1 mM EDTA], affording 300/µg of poly $A^+$ RNA.

This poly $A^+$ RNA was subjected to density gradient centrifugation using 5 to 22% sucrose solutions [RPS 40 Rotor (Hitachi); 15° C., 36 Krpm, 15 hours], giving 16 fractions. mRNA contained in each fraction was precipitated by addition of ethanol, and then dissolved in distilled water to a concentration of 1 µg/µl.

Separately, oocytes were taken out from a mature, female *Xenopus laevis*, and separated into individuals in a modified Barth's culture medium (Colman, A., Transcription and Translation—a practical approach, p291; edited by Hames, B. D. and Higgins, S. J.; IRL Press, 1984).

Each of the mRNA solutions prepared above (70 ng) was injected into one piece of oocyte by means of a capillary and micromanipulator while observing under a microscope. Twenty pieces of oocyte were used for each mRNA sample. Each of the treated oocytes was incubated in 10 µl of modified Barth's medium per oocyte at 20° C. for 36 hours. The supernatant of each culture was centrifuged at 4° C. using an Eppendorf centrifuge at 12000 rpm for 20 minutes, and the supernatant was collected and passed through a gas-sterilized Milipore Filter.

Lymphocytes were collected from the spleen of female C57BL mice (6- to 10-week age) by the usual method, washed twice with RPMI-1640 (containing 2% FCS), and suspended in a medium (RPMI-1640 containing 15% FCS and $5 \times 10^{-5}$M 2-mercaptoethanol) at a cell concentration of $4 \times 10^5$/ml. After LPS (Lipopolysaccharide *E. coli* 0111:B4; Difco Laboratories) was added to a concentration of 50 µg/ml, the resulting cell suspension was put on a 96-well microtiterplate (200 µl in each well), and after 24 hours, each of the culture supernatants of the treated oocytes prepared above was added to each well (20 µl in each). After incubation for four to five days, the number of cells capable of producing $IgG_1$ and the number of cells capable producing $IgG_3$ were measured for each well by the reverse plaque assay (Gronowicz, E., et al., Eur. J. Immunol., 6, 588, 1976). High $IgG_1$ inducing factor activity was observed in fractions 8 and 9 (in the vicinity of 5.5 to 11s) (FIG. 1).

EXAMPLE 3

Preparation of cDNA library.

(1) Preparation of vector primer DNA

Plasmid DNA pSP65 (product of Promega Biotec Inc.) was cleaved with restriction endonucleases EcoRI and Hind III to cut out a polylinker DNA, which in turn was treated with Klenow fragment, followed by coupling, at its both ends, of BamHI linker DNA with its 5'-terminal phosphorylated by $T_4$ DNA ligase, and by cleavage with BamHI, giving a polylinker DNA having BamHI-cut terminals. This polylinker DNA may be replaced by a synthetic nucleotide.

Separately, plasmid DNA $pcDV_1$ (Okayama, H., et al., Mol. Cell. Biol., 3, 280, 1983) was cleaved by restriction endonuclease BamHI at 37° C. for one hour, 30 µl of the reaction mixture thus obtained [containing 2 µg $pcDV_1$, 10 mM Tris-HCl (pH 8.0), 7 mM $MgCl_2$, 2 mM 2-mercaptoethanol, 0.01% bovine serum albumin (BSA), and 6 units of BamHI] was extracted with phenol/chloroform, and ethanol was added to the extract to precipitate DNA. After being washed with ethanol and dried, the precipitate was dissolved in 100 µl of 10 mM Tris-HCl (pH 8.0), 0.4 unit of alkaline phosphatase was added, and the reaction was continued at 60° C. for one hour. The reaction mixture was extracted with phenol/chloroform, and ethanol was added to the extract to precipitate DNA. This DNA (1 µg) and the polylinker DNA obtained above (0.5 µg) were allowed to react in a ligation solution [containing 50 mM Tris-HCl (pH 7.4), 10 mM $MgCl_2$, 10 mM DTT and 1 mM ATP)] at 15° C. for six hours by 5 units of $T_4$ DNA ligase, affording $pcDV_1$ with the polylinker DNA inserted therein ($pcDV_1$-PL). *E. coli* HB101 was transformed with $pcDV_1$-PL obtained above by the known technique (Mandel, et al., J. Mol. Biol., 53, 154, 1970), the strains carrying $pcDV_1$-PL were selected from the transformants, and said plasmid DNA was isolated from these selected strains by the usual method.

$pcDV_1$-PL thus prepared (200 µg) and restriction endonuclease KpnI (350 units) were allowed to react in 400 µl of a reaction mixture [containing 6 mM Tris-HCl (pH 7.5), 6 mM $MgCl_2$, 6 mM 2-mercaptoethanol and 0.02% BSA)] at 37° C. for five hours, the reaction mixture was extracted with phenol/chloroform, and DNA thus extracted was reprecipitated twice by addition of ethanol, washed with 70% ethanol and recovered.

Terminal transferase (TTase) was then allowed to act upon the KpnI-cut ends of the DNA obtained above in 200 µl of a solution [containing 140 mM sodium cacodylate, 30 mM Tris-HCl (pH 6.8), 1 mM $CoCl_2$, 0.1 mM dithiothreitol (DTT), 0.2 mM dTT (containing 4 µCi $^3$H-dTTP) and 108 units of TTase] until dT chain was added to a 45-base length on average, while monitoring the elongation of dT chain by measurement of the incorporation of $^3$H-dTTP at 10-minute intervals. The reaction was terminated by addition of 20 µl of 0.2M EDTA and 10 µl of 10% SDS, and the DNA formed was isolated by extraction with phenol/chloroform and purified by precipitation and washing with ethanol.

This DNA, after being treated with 200 units of restriction endonuclease EcoRI at 37° C. for five hours, was subjected to electrophoresis on 1% agarose gel, and the larger fragment was collected by the DEAE-paper method (Dretzen, G., et al., Anal. Biochem., 112, 295, 1981). This DNA fragment was dissolved in 400 μl of an aqueous solution containing 1M NaCl, 10 mM Tris-HCl (pH 7.4) and 1 mM EDTA, the resulting solution was cooled to 0° C. and absorbed on 0.5 ml oligo-dA column previously equlibrated with an aqueous solution of the same composition as above, and the column was washed with 30 ml of 1M NaCl-TE solution. The absorbed portion was eluted with 65° C. distilled water, the eluate was extracted with phenol/chloroform, and the extracted product was precipitated twice with ethanol, followed by washing with ethanol, giving the objective vector primer DNA.

(2) Preparation of linker DNA

Plasmid DNA pSP-62-PL (product of NEN Inc.) was treated in 20 μl of a solution containing 3 μg pSP-62-PL, 10 mM Tris-HCl (pH 7.5), 7 mM $MgCl_2$, 100 mM NaCl, 7 mM 2-mercaptoethanol, 0.01% BSA, 40 units of XbaI and 6 units of HindIII at 37° C. for two hours to cleave XbaI and HindIII cleavage sites in the polylinker section of pSP-62PL DNA. After incubation, 4 μl of a solution containing dATP, dCTP, dGTP and dTTP (2 mM each) and 3 units of klenow fragment were added, and the mixture was held at 20° C. for 30 minutes. The reaction mixture was extracted with phenol/chloroform, ethanol was added to the extract to precipitate DNA, and 250 ng of this DNA was allowed to react with 5 units of $T_4$ DNA ligase in 10 μl of a ligation solution [containing 50 mM Tris-HCl (pH 7.4), 10 mM $MgCl_2$, 10 mM DTT and 1 mM ATP] at 15° C. for 6 hours to effect cyclization. The circular DNA thus prepared was used for transformation of E. coli HB101. Of the transformants selected by using ampicillin resistance as marker, those strains which contain plasmid DNA deficient in the section from HindIII-recognition site to SalI-recognition site in the pSP-62-PL polylinker were screened out, and said DNA was isolated from these strains by the usual method.

The plasmid DNA thus isolated was treated with restriction endonuclease SalI at 37° C. for two hours. 30 μl of the resulting reaction mixture [containing 2 μg of plasmid DNA, 10 mM Tris-HCl (pH 7.5), 7 mM $MgCl_2$, 175 mM NaCl, 0.2 mM EDTA, 7 mM 2-mercaptoethanol, 0.01 % BSA and 16 units of SalI] was mixed with 5 μl of a solution containing dATP, dCTP, dGTP and dTTP (2 mM each) and 3 units of Klenow fragment, the reaction was continued at 20° C. for 30 minutes, the reaction mixture was extracted with phenol/chloroform, and ethanol was added to the extract to precipitate DNA.

This DNA (2 μg) and HindIII linker DNA with its 5'-end phosphorylated (0.45 μg) were allowed to react in 20 μl of the same ligation solution as used above at 15° C. for 20 hours by addition of 20 units of $T_4$ DNA ligase, and the product was employed to transform E. coli HB101. Of the transformants thus formed, those strains containing plasmid DNA in which SalI-recognition site had been lost and HindIII-recognition site had been newly created were screened out, and said plasmid DNA was isolated from these strains by the known technique (pSP-62-K2 in FIG. 2).

pSP-62-K2 (100 μg) and SacI (120 units) were allowed to react in 400 μl of a reaction mixture [containing 10 mM Tris-HCl (pH 7.5), 7 mM $MgCl_2$ and 7 mM 2-mercaptoethanol] at 37° C. for 1.5 hours, and the reaction mixture was extracted with phenol/chloroform, and the DNA thus extracted was precipitated by addition of ethanol and washed with ethanol.

The DNA isolated above (100 μg) was allowed to react in a solution [containing 140 mM sodium cacodylate, 30 mM Tris-HCl (pH 6.8), 1 mM $CoCl_2$, 0.1 mM DTT, 0.1 mM GTP (containing 2 μCi $^3$H-dGTP) and 27 units of TTase] at 37° C. for 20 minutes until dG chain of 14-base length on average was added to the SacI-cut end. The reaction was terminated by addition of 0.2M EDTA and 5 μl of 10% SDS, the reaction mixture was extracted with phenol/chloroform, and the DNA thus extracted [(I) in FIG. 2] was precipitated by addition of ethanol and washed with ethanol.

The DNA thus isolated was allowed to react in a solution containing 10 mM Tris-HCl (pH 7.5), 7 mM $MgCl_2$, 60 mM NaCl and 50 units of HindIII at 37° C. for two hours, the reaction mixture was subjected to electrophoresis on 1.5% agarose gel, and the smaller fragment (approximately 500 base pairs) was collected by the DEAE-paper method, affording the objective linker DNA.

(3) Synthesis of cDNA

Reverse transcriptase was added to a mixture of poly $A^+$ RNA (3 μg) obtained in Example 2 and vector primer (0.7 μg) prepared in (1) above in 20 μl of a solution containing 50 mM Tris-HCl (pH 8.3), 8 mM $MgCl_2$, 30 mM KCl, 0.3 mM DTT, 2 mM dNTP (dATP, dGTP, dCTP and dTTP each) and 10 μCi a-$^{32}$P-dCTP, the reaction was continued while monitoring the incorporation of $^{32}$P-dCTP, and the reaction mixture was worked up in the same manner as above (termination, extraction, reprecipitation and washing).

The DNA thus obtained was subjected to the same manner as above for the elongation of dT or dG chain to obtain the DNA to which dC chain of a 14-base length on average was added.

The DNA thus obtained was treated with 5 units of HindIII in a reaction mixture containing 6 mM Tris-HCl (pH 7.5), 6 mM of $MgCl_2$, 6 mM 2-mercaptoethanol, 50 mM NaCl and 0.01% BSA at 37° C. for one hour, and the reaction mixture was worked up in a similar manner, giving DNA shown in (II) of FIG. 2.

This DNA and the linker DNA obtained in (2) above were allowed to react in 100 μl of a solution [containing 20 mM Tris-HCl (pH 7.5), 4 mM $MgCl_2$, 10 mM $(NH_4)_2SO_4$, 0.1M KCl, 0.1 mM β-NAD, 0.01% BSA and 0.6 μg of E. coli DNA ligase] overnight at 12° C. The following components were then added at respective specified concentrations [dATP, dCTP, dGTP and dTTP to 40 μM each; β-NAD to 0.15 mM; E. coli DNA ligase (0.4 unit); E. coli DNA polymerase (0.3 unit); and E. coli RNase H (1 unit)], and the resulting mixture was allowed to react at 12° C. for one hour and at 25° C. for one hour, affording a solution containing the objective plasmid carrying cDNA. This solution was submitted to the next step without any treatment.

(4) Preparation of cDNA library

Competent cells of E. coli HB101 were transformed with the cDNA-containing plasmid DNA obtained in (3) above by the known technique, giving cDNA library. From this library were separated 16 groups, each composed of 250 independent transformants.

EXAMPLE 4

In-vitro transcription (1) Preparation of template DNA and selection of restriction endonuclease In transcription with SP6 polymerase, it is necessary to cut DNA at a position downstream the cDNA section in order to ensure transcription termination.

To this end, the cDNA cloning vector of this invention has the polylinker inserted at a position downstream the cDNA section. Selection of suitable restriction endonuclease was performed as described below.

Plasmid DNA, isolated from the cDNA library obtained in (4) of Example 3 in the same manner as above, was treated with PstI, SacI and SalI each, and the resulting DNAs obtained by extraction with phenol/chloroform, followed by precipitation and washing with ethanol, were used as template in the in-vitro transcription process detailed in (2) below.

After the transcription, the IgG$_1$ inducing factor activity was screened in the same manner as in Example 2, the result of which is summarized in Table 1. As is apparent from the table, SalI was found to be the suitable restriction endonuclease for the purpose. Hence, the DNA prepared by treatment with this enzyme was adopted as template DNA for in-vitro transcription.

(2) In-vitro transcription

The components given below were quickly mixed in that order, and the mixture was held at 40° C. for one hour to complete the reaction.

| 1 | Pure water (distilled twice) | 19.3 μl |
|---|---|---|
| 2 | Transcription buffer | 10 |
| 3 | 1M DTT | 0.5 |
| 4 | Ribonuclease inhibitor (70 units/μl) | 0.7 |
| 5 | γNTPs | 4 |
| 6 | 10mM m$^7$G(5')ppp(5')G | 5 |
| 7 | 1 mg/ml BSA | 5 |
| 8 | Template DNA (1 μg/ul) | 3 |
| 9 | α-$^{32}$P-GTP (10000 cpm/μl) | 2 |
| 10 | SP6 RNA polymerase (15 units/μl) | 0.5 |
|   | Total: | 50 μl | wherein transcription buffer is [200 mM Tris-HCl (pH 7.5), 30 mM MgCl$_2$ and 10 mM spermidine]; γNTPs is [2.5 mM ATP, CTP, GTP and UTP]; and m$^7$G(5')ppp(5')G is an analogue of cap structure of eukaryote mRNA (product of P-L Biochemicals)—a compound composed of two units of GTP linked together at 5' ends, with the guanine at one end methylated at 7-position.

The synthetic mRNA thus formed was isolated from the substrate γNTPs by gel filtration technique as described below.

A disposable syringe (1 ml capacity) was charged with Sephadex G-50 (Pharmacia) previously equilibrated with TE buffer [containing 10 mM Tris-HCl (pH 8.0) and 1 mM EDTA (pH 8.0)]. The reaction mixture obtained above was applied to this column, and the synthetic mRNA was recovered in the eluate after centrifugation at 1300 rpm for four minutes. Counting the $^{32}$P contained in the eluate showed that 1.5 to 2.5 μg of the synthetic mRNA could be isolated.

The crude product thus collected was extracted with phenol, precipitated with ethanol and dried, and the purified product was dissolved in distilled water (0.3 μg/μl).

EXAMPLE 5

Screening of IgG$_1$ inducing factor cDNA cDNA-containing plasmid DNA was taken out from each of the 16 groups of cDNA library (each group consisting of about 250 independent transformants), and cleaved with SalI to produce a template DNA, which was used for the synthesis of mRNA by in-vitro transcription. Each of the synthetic mRNAs thus obtained was adjusted to a concentration of 0.3 μg/μl and injected into oocytes of *Xenopus laevis*, and the culture supernatant was examined for IgG$_1$ inducing factor activity.

The cDNA plasmid of one group (No. 3) out of the three groups found to have the inducing factor activity was used to transform *E. coli* HB101, 400 clones were randomly picked out, and each of these was cultured in 0.5 ml of L broth (Luria's medium) containing 30 μg/ml ampicilin. 20-μl samples, taken out from 25 clones each, were put together, thereby preparing a total of 16 groups (each containing 25 clones). Plasmid screening was conducted with these 16 groups in the same manner as for the 250 groups, finding the IgG$_1$ inducing factor activity in two groups.

Plasmid DNA was collected from all the clones of these two groups (25×2), and screened in the same manner as above. One plasmid in each of the two groups (a total of two plasmids) showed the IgG$_1$ inducing factor activity.

EXAMPLE 6

Preparation of IgG$_1$ inducing factor DNA

The two plasmids isolated above carrying the IgG$_1$ inducing factor cDNA were named pSP6K-IIF 293 and pSP6K-IIF 374, respectively. These two plasmids showed the same restriction endonuclease cleavage map; hence, pSP6K-IIF 374 was used to transform *E. coli* HB101 by the usual method, the transformants thus obtained (or the clones carrying the IgG$_1$ inducing factor cDNA plasmid of Example 5) were cultured in L broth at 37° C. by shaking until the cell concentration reached 8×10$^8$/ml, and plasmid pSP6K-IIF 374 DNA was isolated from the cultured cells by the known technique (yield: 2 mg from one liter of culture solution).

EXAMPLE 7

Determination of the structure of IgG$_1$ inducing factor cDNA pSP6K-IIF 374 was cleaved with restriction endonuclease BamHI, the reaction mixture was subjected to electrophoresis, and a fragment containing the IgG$_1$ inducing factor cDNA was isolated by the DEAE-paper method. The restriction endonuclease cleavage map of this fragment is shown in FIG. 3. It was then treated with the enzymes shown in FIG. 3, each fragment was cloned using M13 phage vector, and the nucleotide sequence of each fragment was determined by the dideoxy chain termination method [Sanger, F., et al., *Proc. Nat. Acad. Sci.* USA, 74, 5463 (1977)]. The sequencing direction and range are illustrated by the arrow marks at the bottom of FIG. 3.

The nucleotide sequence of the IgG$_1$ inducing factor cDNA thus determined and the presumed amino acid sequence of said factor are shown in FIG. 4.

The IgG$_1$ inducing factor, which is a secretary protein, is considered to have a signal peptide on the N-terminal side. Judging from the hydrophobicity of said factor and comparison with known signal peptides, it may be deduced that No. 1 through No. 15 (or No. 1 through No. 24) amino acids constitute the signal peptide to be released later.

TABLE 1

IgG₁ Inducing Factor Activity by
Culture of Mouse Splenic Lymphocytes

| Additive to lymphocyte culture | % | DNA used as template | Number of plaqueforming cells in culture | |
|---|---|---|---|---|
| | | | IgG₁ | IgG₃ |
| Oocyte culture supernatant | 10 | DNA obtained by cutting cDNA with SalI | 175 | 218 |
| | 20 | | 490 | 396 |
| Oocyte culture supernatant | 10 | DNA obtained by cutting cDNA with SacI | 12 | 110 |
| | 20 | | 53 | 218 |
| Oocyte culture supernatant | 10 | DNA obtained by cutting cDNA with PstI | 17 | 898 |
| | 20 | | 17 | 370 |
| Phosphate buffer | 10 | None | 22 | 257 |
| | 20 | | 43 | 658 |
| None | 0 | None | 17 | 749 |
| | 0 | | 26 | 782 |
| B6.C-H-2$^{bm12}$ 2.19 T cells | 5 | None | 1516 | 101 |

BRIEF DESCRIPTION OF THE DRAWINGS

- Culture supernatant of oocytes into which all the poly A⁺ RNA derived from 2.19 T cells have been injected
- P: Culture supernatant of oocytes into which PBS (phosphate buffer saline) has been injected
- T: Culture supernatant of 2.19 T cells
- M: Poly A⁺ RNA of myeloma TEPC15
- C: Nothing added

FIG. 4 shows the nucleotide sequence in cDNA of IgG₁ inducing factor and the amino acid sequence of said factor.

Figure 1:
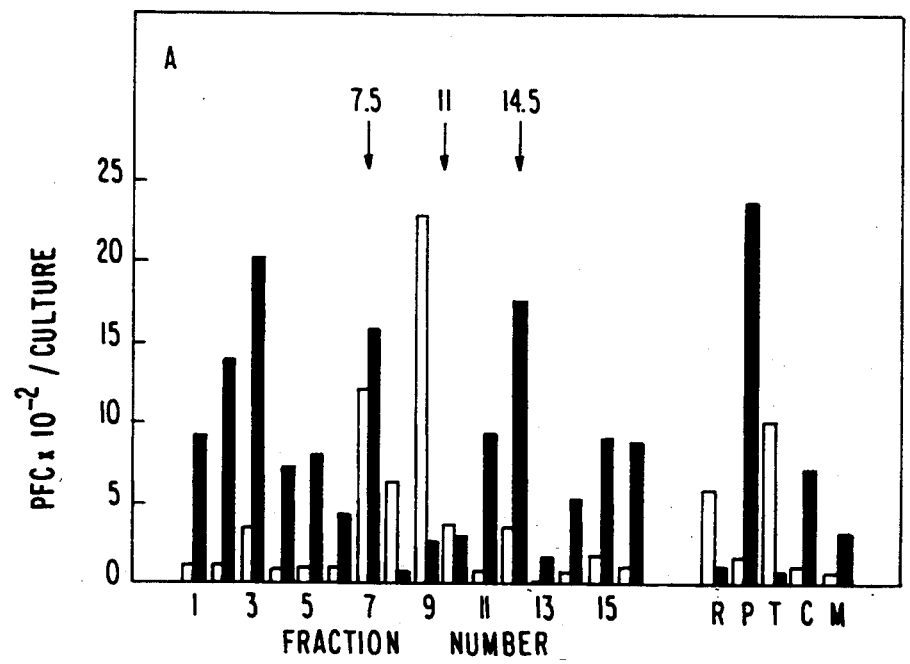
FIG. 1 shows the IgG₁ inducing factor activity of 16 fractions of poly A⁺ RNA (A) and the absorbance at 260 nm of these fractions (B), in which the white bar represents the number of IgG₁ producing cells, the black bar expresses the number of IgG₃ producing cells, and the numeral above each arrow mark denotes sedimentation constant S. R, P, T, M and C are.
Figure 3:
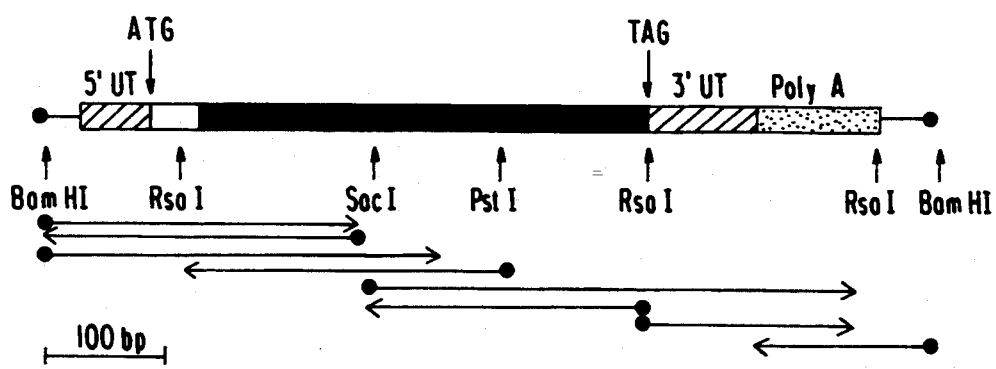
FIG. 3 is the restriction endonuclease cleavage map of cDNA-containing BamHI fragment in pSP6K-IIF 374, in which the arrow marks show the sequencing direction and range.
Figure 2:
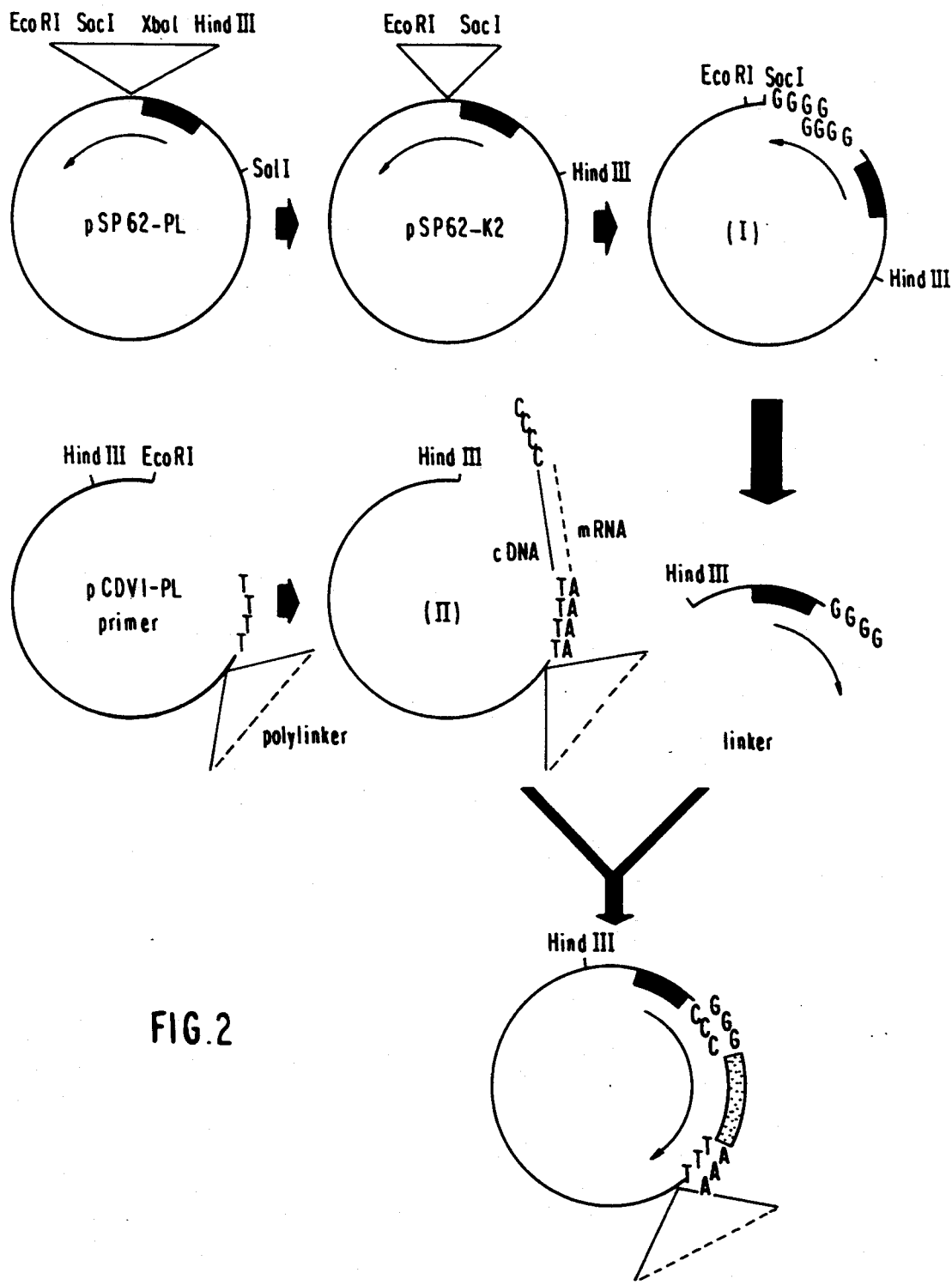
FIG. 2 is a diagram illustrating SP6 vector library construction.

What is claimed is:

1. A DNA molecule coding for a mouse polypeptide possessing the biological activity of mouse IL-4, wherein said biological activity is the induction of IgG₁ production.

2. The DNA molecule of claim 1, wherein said polypeptide has the following amino acid sequence:

Cys Asp Lys Asn His Leu Arg Glu Ile Ile Gly Ile Leu
Asn Glu Val Thr Gly Glu Gly Thr Pro Cys Thr Glu Met
Asp Val Pro Asn Val Leu Thr Ala Thr Lys Asn Thr Thr
Glu Ser Glu Leu Val Cys Arg Ala Ser Lys Val Leu Arg
Ile Phe Tyr Leu Lys His Gly Lys Thr Pro Cys Leu Lys
Lys Asn Ser Ser Val Leu Met Glu Leu Gln Arg Leu Phe
Arg Ala Phe Arg Cys Leu Asp Ser Ser Ile Ser Cys Thr
Met Asn Glu Ser Lys Ser Thr Ser Leu Lys Asp Phe Leu
Glu Ser Leu Lys Ser Ile Met Gln Met Asp Tyr Ser

3. The DNA molecule of claim 1, wherein said polypeptide has the following amino acid sequence:

Glu Cys Thr Arg Ser His Ile His Gly Cys Asp Lys Asn
His Leu Arg Glu Ile Ile Gly Ile Leu Asn Glu Val Thr
Gly Glu Gly Thr Pro Cys Thr Glu Met Asp Val Pro Asn
Val Leu Thr Ala Thr Lys Asn Thr Thr Glu Ser Glu Leu
Val Cys Arg Ala Ser Lys Val Leu Arg Ile Phe Tyr Leu
Lys His Gly Lys Thr Pro Cys Leu Lys Lys Asn Ser Ser
Val Leu Met Glu Leu Gln Arg Leu Phe Arg Ala Phe Arg
Cys Leu Asp Ser Ser Ile Ser Cys Thr Met Asn Glu Ser
Lys Ser Thr Ser Leu Lys Asp Phe Leu Glu Ser Leu Lys
Ser Ile Met Gln Met Asp Tyr Ser

4. The DNA molecule of claim 1, wherein said polypeptide has the following amino acid sequence:

Met Gly Leu Asn Pro Gln Leu Val Val Ile Leu Leu Phe
Phe Leu Glu Cys Thr Arg Ser His Ile His Gly Cys Asp
Lys Asn His Leu Arg Glu Ile Ile Gly Ile Leu Asn Glu
Val Thr Gly Glu Gly Thr Pro Cys Thr Glu Met Asp Val
Pro Asn Val Leu Thr Ala Thr Lys Ash Thr Thr Glu Ser
Glu Leu Val Cys Arg Ala Ser Lys Val Leu Arg Ile Phe
Tyr Leu Lys His Gly Lys Thr Pro Cys Leu Lys Lys Asn
Ser Ser Val Leu Met Glu Leu Gln Arg Leu Phe Arg Ala
Phe Arg Cys Leu Asp Ser Ser Ile Ser Cys Thr Met Asn
Glu Ser Lys Ser Thr Ser Leu Lys Asp Phe Leu Glu Ser
Leu Lys Ser Ile Met Gln Met Asp Tyr Ser

5. The DNA molecule of claims 1, 2 and 3, wherein said molecule additionally has the translational start sequence ATG at the 5'-terminus thereof.

* * * * *